United States Patent
van Haveren et al.

(10) Patent No.: US 9,284,290 B2
(45) Date of Patent: Mar. 15, 2016

(54) PROCESS FOR THE PRODUCTION OF THE MIXTURE 2,4 FURANDICARBOXYLIC ACID (FDCA) AND 2,5 FURANDICARBOXYLIC ACID VIA DISPROPORTIONATION REACTION

(75) Inventors: Jacco van Haveren, Ede (NL); Shanmugam Thiyagarajan, Wageningen (NL); Augusto Teruo Morita, São Bernardo do Campo, SP (BR)

(73) Assignee: Braskem S.A., Camacari, BA (BR)

( * ) Notice: Subject to any disclaimer, the term of this patent is extended or adjusted under 35 U.S.C. 154(b) by 0 days.

(21) Appl. No.: 14/368,676

(22) PCT Filed: Dec. 29, 2011

(86) PCT No.: PCT/BR2011/000502
§ 371 (c)(1),
(2), (4) Date: Dec. 8, 2014

(87) PCT Pub. No.: WO2013/096998
PCT Pub. Date: Jul. 4, 2013

(65) Prior Publication Data
US 2015/0119588 A1 Apr. 30, 2015

(51) Int. Cl.
*C07D 307/34* (2006.01)
*C07D 307/68* (2006.01)
*C08G 63/181* (2006.01)

(52) U.S. Cl.
CPC ............ *C07D 307/68* (2013.01); *C08G 63/181* (2013.01)

(58) Field of Classification Search
CPC ...................................................... C07D 307/34
USPC .................................................. 549/429, 485
See application file for complete search history.

(56) References Cited

PUBLICATIONS

Irwin A. Pearl, "Reactions of Vanillin and Its Derived Compounds. III. The Cannizzaro Reaction of Vanillin", Contribution/The Institute of Paper Chemistry, Jun. 24, 1946.
Toshiyuki Shono et al., The Journal of the Society of Chemical Industry, Japan, vol. 63 (1960) No. 1, pp. 176-178.
Henry Gilman et al., "Orientation in the Furan Nucleus. VI. ss-Substituted Furans", Contribution/Chemical Laboratory of Iowa State College, Jul. 6, 1933.
European Patent Office, International Search Report of PCT/BR2011/000502, Dec. 21, 2012.

*Primary Examiner* — Golam M M Shameem
(74) *Attorney, Agent, or Firm* — Duane Morris LLP

(57) ABSTRACT

The present invention refers to a process for production of a mixture including 2,4-furandicarboxylic acid (2,4-FDCA) and 2,5 furandicarboxylic acid (2,5-FDCA) through the disproportionation route, using as base compounds oxidation products of furfural. This invention also relates to a process for production of 2,4-FDCA as a result of a disproportionation route and the use of 2,4-FDCA as a monomer or comonomer to synthesize esters or any compounds which can generate macromolecules, such as polyesters.

9 Claims, 3 Drawing Sheets

PROCESS FOR THE PRODUCTION OF THE MIXTURE 2,4 FURANDICARBOXYLIC ACID (FDCA) AND 2,5 FURANDICARBOXYLIC ACID VIA DISPROPORTIONATION REACTION

FIELD

The present invention refers to the production of 2,4-furandicarboxylic acid (2,4-FDCA) through the disproportionation route, using as base compounds oxidation products of furfural. This invention also refers to the mixture comprising 2,5-FDCA and 2,4-FDCA as a result of a disproportionation route and the use of 2,4-FDCA as a monomer or comonomer to produce macromolecules.

BACKGROUND

There is a huge interest in using furandicarboxylic acids as a monomer to produce polymers. So far, this has been completely focused on 2,5 furandicarboxylic acid (2,5-FDCA), the monomer for the production of PEF (poly(ethylene 2,5-furandicarboxylate)) and other polymers. This resin has been considered as one of the potential substitutes for PET (polyethylene terephthalate) because it offers similar properties and can be produced from renewable sources. The potential of 2,4-furandicarboxylic acid up to now has been overlooked by researchers, only a few production routes have been described.

The article "*Reaction of Vanillin and its Derived Compounds. XIV. 2,4-Furanedicarboxylic Acid from Vanillin*" (Pearl et al.) mentions Feist et al., where the production of 2,4-FDCA from methyl coumalate was explained. However, that precursor is much more expensive than furoic acids. The use of vanillin is also analyzed in the paper, but the yield was less than 3%. The reaction medium for the synthesis from vanillin is very complex.

Hachihama et al. describes, in "*Syntheses of Polyesters containing Furan Ring*", the synthesis of 2,4-FDCA through a four-step process, starting from 2 moles of malic acid, via methylcoumalate, in an overall yield less than 15% and without valuable byproduct formation. The approach starting from malic acid does not only result in a very low yield but also comprises steps that require stoichiometric reagents like HBr and several complex and different solvent systems like sulphuric acid, methanol and chloroform.

The article also describes one example of a 2,4-FDCA based polyester. The melting point of that polymer is lower than that of 2,5-FDCA based ones, but the data supplied are excessively limited to draw any conclusion about the potential properties of that resin.

The Italian article "*Ricerche sulla migrazione del gruppo carbossilico nei sistemi eterociclici—Nota I. Sulfa preparazione dell'acido 2-5-furandicarbossilico da acido furoico*" (Andrisano et al.) describes the synthesis of 2,5-FDCA through the disproportionation route.

Andrisano et al reported that the potassium salt of furoic acid when heated up to 250-300° C. in nitrogen atmosphere, undergoes decarboxylation to furan with simultaneous carboxylation at the 5-position to dipotassium 2,5 furandicarboxylate.

This disproportionation reaction subsequently has been overlooked in the recent attention for developing renewable routes to 2,5-FDCA. That this route should have potential is nonetheless clear from the disproportionation or thermal rearrangement of alkaline salts of aromatic carboxylates to symmetrical aromatic dicarboxylates. This reaction is known as the Henkel reaction (also called Raecke process) and is usually carried out in the presence of cadmium or other metal salts. As mentioned before, this process yields symmetrical aromatic dicarboxylates (which can be acidified to yield dicarboxylic acids). Thus, it is highly unexpected that the disproportionation of K-furoate yields an asymmetrical compound like the 2,4-FDCA.

Therefore, considering the problems of low yield, excessive number of process steps, presence of undesired byproducts and the cost of the reagents, the objective of this invention is to provide a route to synthesize 2,4-FDCA in a 2-step process from cheap biomass (products derived from furfural), with elevated yield and absence of toxic byproducts. Up to now there has been little research on the properties of the 2,4-FDCA based polyester, and virtually no studies analyzing its impacts as comonomer in PEF or other polymers and products. The combination of those 2,5-FDCA and 2,4-FDCA monomers might generate a synergic effect such as that of ethylene terephthalate and ethylene isophthalate in the macromolecular structure and properties of PET such as crystallization and melting point.

SUMMARY

The objective of this invention is to provide a process for producing a mixture of 2,4-FDCA and 2,5-FDCA by subjecting furoic acid salts to a disproportionation reaction, catalysed by metal salts, comprising the steps of:

a) Oxidizing furfural compounds in the presence of catalysts and alkaline solution in order to obtain biobased furoic acid salts;

b) Heating the furoic acid salts under stirring in the presence of a metal based catalyst and cooling the reaction mixture until room temperature;

c) Collecting the furan obtained in item (b) in order to obtain the mixture of 2,4-FDCA and 2,5-FDCA;

d) Optionally, filter off the black insoluble material of the reaction mixture obtained in item (c) and acidifying the reaction mixture in order to collect the 2,5-FDCA;

e) Optionally, subjecting the mixture obtained in item 1 (c), to an extraction or other separation method in order to purify 2,4-FDCA.

The object of this invention also comprises the mixture of 2,5-FDCA and 2,4-FDCA as a result of a disproportionation route, the 2,4-FDCA obtained by the disproportionation reaction process and the use of 2,4-FDCA to synthesize chemical compounds which can be polymerized such as esters is also object of this invention.

DETAILED DESCRIPTION

Figure 1:
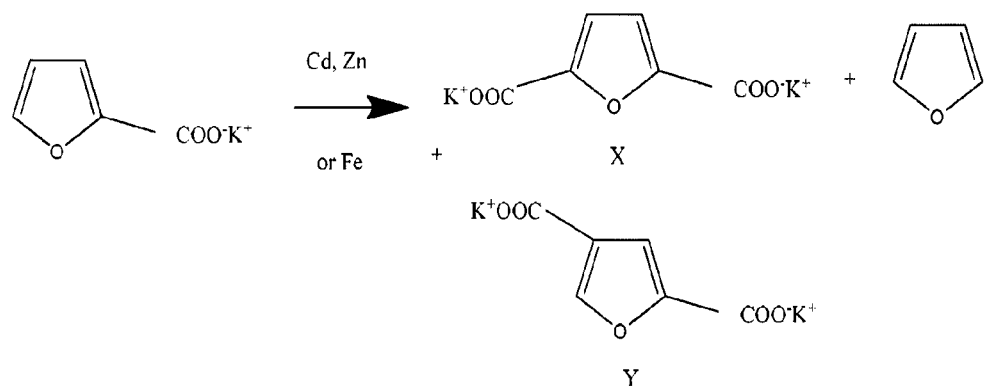
FIG. 1: Disproportionation reaction undergone by the K-furoate generating the mixture of dicarboxylic acids precursors (which will further be acidified) and furan.

The objective of this invention is to provide a process for producing a mixture of 2,4-FDCA and 2,5-FDCA by subjecting furoic acid salts to a disproportionation reaction (see FIG. 1), catalyzed by metal salts, comprising the steps of:

a) Oxidizing furfural compounds in the presence of catalysts and alkaline solution in order to obtain biobased furoic acid salts;

b) Heating the furoic acid salts under stirring in the presence of a metal based catalyst and cooling the reaction mixture until room temperature;

c) Collecting the furan obtained in item (b) in order to obtain the mixture of 2,4 FDCA and 2,5-FDCA;

d) Optionally, filter off the black insoluble material of the reaction mixture obtained in item (c) and acidifying the reaction mixture in order to collect the 2,5-FDCA;

e) Optionally, subjecting the mixture obtained in item 1 (c), to an extraction or other separation method in order to purify 2,4-FDCA.

The furfural oxidation of the first step is made in the presence of $Au/TiO_2$ catalyst. The $Au/TiO_2$ is optimized for this reaction. Furfural, $Au/TiO_2$ and NaOH in water was charged into the reactor and pressurized with oxygen ($3 \times 10^5$ Pa of $O_2$) and stirred at 600 rpm and at 50° C. for 3-5 h. The furoic acid product is further converted to a furoic acid salt, which can be potassium, sodium, cesium and preferably potassium. Other renewable sources can be used to produce the furoates. Catalysts selected from the group consisting of Au/C, Au/ZnO, $Au/Fe_2O_3$ or other Au catalysts may also be used.

The furoic acid salt and a metal salt catalyst are then heated under stirring for an interval ranging from 1 h to 5.5 h, preferably 5 h. The temperature of the system ranges from 220° C. to 280° C., preferably 260° C. (salt bath temperature not the internal temperature.) The catalyst is chosen from transition metal salts, alkaline earth metal salts, preferably $FeCl_2$, $CdI_2$, $Zn(OTf)_2$ or $ZnCl_2$. When the $FeCl_2$ catalyst is used, the reactive mixture is placed under a slight flow of $N_2$. Among the wide range of catalysts used, $ZnCl_2$ (20 mole %) was found to be active (best) and the results obtained are comparable or more even better than the $CdI_2$ catalyst which has been screened as the best catalyst by Andrisano for the disproportionation reaction of K-Furoate.

The reaction was stopped after the specified time and cooled down to room temperature in 2 h. The furan is collected via a Dean-Stark trap and a $CO_2$-aceton-ice bath. After cooling, water is added and the black insoluble material is filtered off and upon acidification the 2,5-FDCA was collected. 12 N HCl is used to acidify the reaction mixture until reaches pH 1. 2,5-FDCA is precipitated out immediately from the reaction mixture. NMR analysis shows that there is a high degree of K-furoate conversion which allows to precise the amount of 2,4-FDCA in the product mixture.

The use of the process described herein allows 2,4-FDCA yields of at least 7 wt %, preferably at least 15 to 20 wt %, more preferably 32 wt % at least (the remaining fraction of the products is basically 2,5-FDCA). Furthermore, the present invention presents the following advantages:

Production of 2,4-FDCA from furoates derived from cheap and renewable stock feed, e.g. furfural Production of 2,4-FDCA through a simple 2-step process which produces no harmful, toxic or undesirable byproducts (the main byproduct furan has actually highly interesting applications)

The use of an iron catalyst, cheaper than the usual metals catalysts and environmentally more benign.

The diacid obtained with the present invention may be useful to produce chemical compounds which can be useful monomers to the polymer industry and other industries such as solvents, lubricants or plasticizers industry. Furthermore, these 2,4-FDCA based compounds can be used to produce polyesters.

The following examples illustrate the present invention, however not limiting the scope of the invention

EXAMPLE 1

Procedure for Preparing Furoic Acid from Furfural: Oxidation of Furfural

Furfural (3.00 grammes, 31.22 mmol) was dissolved in 40 ml water. One equivalent (31.75 mmol; 1.02 eq) of base (NaOH) and 0.012 grammes of Au/TiO2 catalyst (ex-Strem-Autek; 1.2 wt % Au, Au particle size 2-3 nm) were added to the furfural solution in water. The 100 ml reaction vessel (Büchi glasuster picoclave) was closed and overhead stirring was applied. Oxygen pressure (303974.99 Pa of $O_2$) was applied to the reaction mixture. The reaction mixture was put at 50° C. After one hour reaction the pressure has dropped to approximately one atmosphere and the reaction vessel was repressurised to 303974.99 Pa of $O_2$ and subsequently stirred overnight. After overnight stirring the reaction was stopped and the catalyst was filtered off. The solvent (water) was removed by a rotary evaporator and applying vacuum. The yield of sodium furoate was 94.9%.

The use of gold catalysts in the above reaction often is a little bit more selective than other metal based catalysts such as Pt or Pd and under the circumstances used in the reaction, the combination of a heterogeneous catalyst that acts under the same basic conditions required for the subsequent disproportionation reaction is advantageous.

Figure 2:
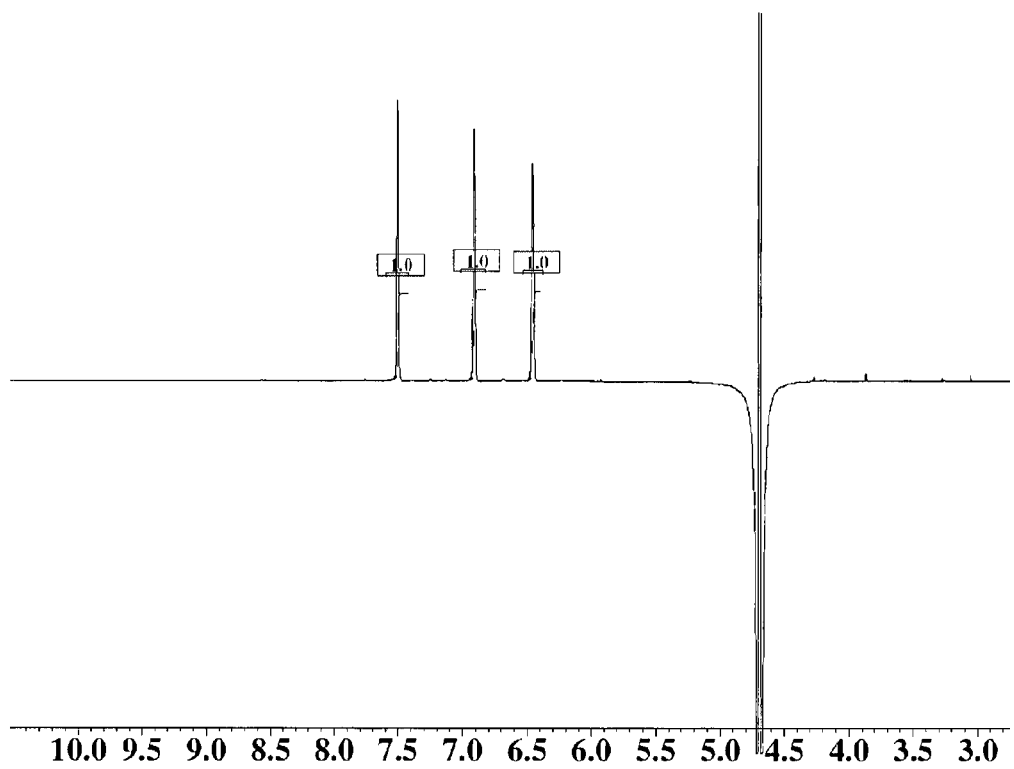
FIG. 2: H NMR analysis showing the three protons for furoate in equal ratio, without any other signal besides the NMR solvent, confirming that the furfural had been converted completely and selectively into sodium furoate.

H NMR analysis (see FIG. 2) showed the three protons for furoate in equal ratio, without any other signal besides the NMR solvent, confirming that the furfural had been converted completely and selectively into sodium furoate. In the absence of base no reaction is occurring.

This reaction demonstrates the efficiency in obtaining furoate salts from furfural, that can serve as input for the subsequent disproportionation reaction.

EXAMPLE 2

Process for Production of a Mixture of 2,4-FDCA and 2,5-FDCA 6.00 grams of K-furoate (39.95 mmol) and 2.20 grams of $CdI_2$ (6.01 mmoles) were grinded together well and charged into a 3-necked flat flange reaction vessel. The mixture was then heated in a salt bath at 265° C. with stirring using a mechanical overhead stirrer under continuous (very slow) flow of nitrogen. During the course of reaction, the furan formed was collected via a Dean-Stark trap and an $CO_2$/Acetone ice bath (−78° C.), yielding furan of 1.35 grams (95% of the theoretical amount). After 4 hours, the reaction was stopped and allowed to cool down at room temperature for 1 h. Thus obtained black hard solid substance was dissolved in water (50 mL). A residual amount of water insoluble black material was filtered off and the deep yellow colour filtrate was acidified using 12 N HCl (until pH:1). 2,5-FDCA was precipitated and filtered off. 60.9% of the theoretical amount of 2,5-FDCA was isolated. NMR analysis of the reaction mixture after filtering off the insoluble black material showed that the K-furoate had been converted over 90% and that there is a mixture being present of 2,4-FDCA and 2,5-FDCA, in a ratio of 0.32:0.68. Based upon this and the 60.9% of 2,5-FDCA isolated, it can be calculated that the K-furoate has been disproportionated into a mixture of furandicarboxylic acids in 89% of the theoretical yield.

EXAMPLE 3

Process for Production of a Mixture of 2,4-FDCA Followed by 2,5-FDCA Isolation 5.3 grams of K-furoate (35.4 mmoles) and 0.97 grams (7.65 mmoles) of $FeCl_2$ catalyst were grinded together well and charged into a 3-necked flat flange reaction vessel. The mixture was then heated in a salt bath at 250° C. with stirring using a mechanical overhead stirrer under continuous (very slow) flow of nitrogen. During the course of reaction, the furan formed was collected via a Dean-Stark trap and an CO2-aceton-ice bath (−78° C.). After 5.5 hours, the reaction was stopped and allowed to cool down at room temperature for 1 h. Thus obtained black hard solid substances were dissolved in water (45 mL). A residual amount of water insoluble black material was filtered off and the deep yellow colour residue was acidified using 12 N HCl (until pH:1). 2,5 FDA was precipitated and filtered off. 60.9% of the theoretical amount of 2,5 FDA was isolated. NMR analysis of the reaction mixture after filtering off the insoluble black material showed that the K-furoate had been disproportionated over 81% and that there is a mixture being present of 2,4-FDCA and 2,5-FDCA, in a ratio of 0.21:0.79. Based upon this and the 60.9% of 2,5-FDCA isolated, it can be calculated that the K-furoate has been disproportionated into a mixture of furandicarboxylic acids in 75% of the theoretical yield.

EXAMPLE 4

Procedure for Purification of 2,4-Furandicarboxylic Acid

Figure 3:
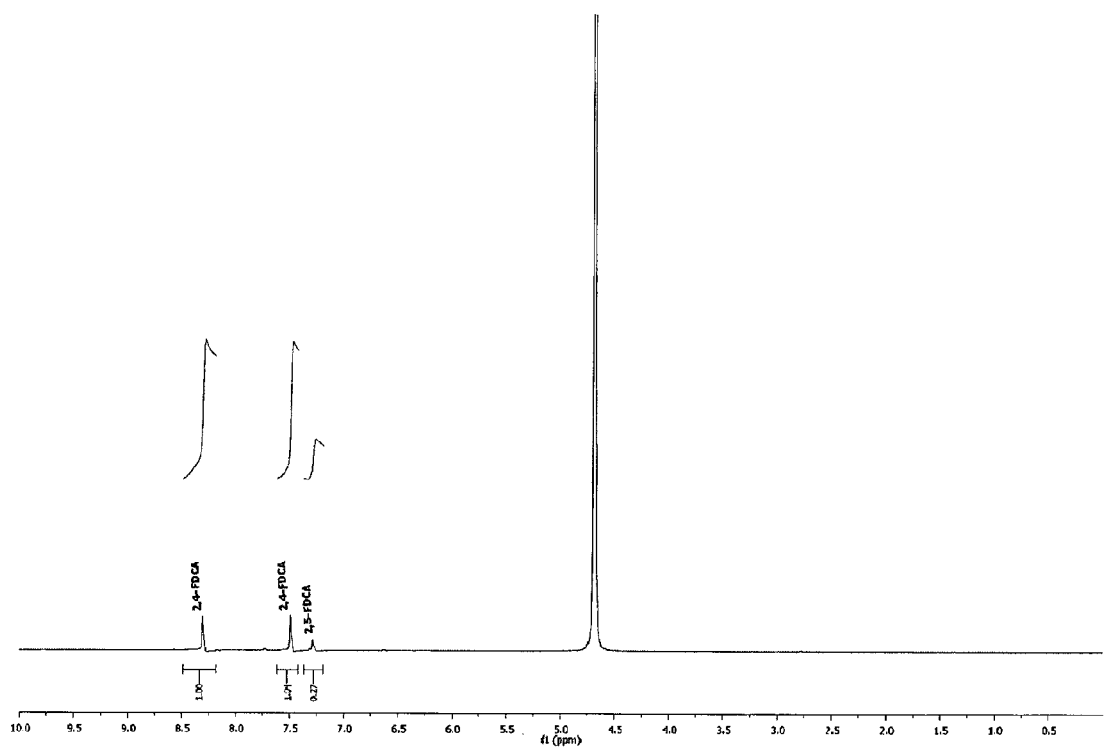
FIG. 3: H NMR spectrum of 85% pure 2,4-FDCA (the signal at 4.7 ppm is HDO)

The reaction crude mixture (2,4-FDCA, 2,5-FDCA, 2-Furoic acid and $CdI_2$) was subjected to soxhlet extraction using acetone for 8 h. After cooling to room temperature, acetone insoluble white crystalline powder was analyzed by NMR which showed no proton signals. The acetone soluble part was recovered and the solvent was evaporated under reduced pressure in the rotatory evaporator. NMR analysis showed the presence of 2,4-FDCA, 2,5-FDCA and 2-Furoic acid in the crude mixture. The mixture was then stirred vigorously with chloroform for 10 min at room temperature and filtered. This process was repeated until 2-furoic acid was completely removed from the mixture. The product was then dried in a vacuum oven at 40° C. for 12 h. As the solubility difference of 2,4-FDCA was comparatively high in acetone at room temperature, the same technique (adapted with chloroform previously) was repeated with acetone to separate the 2,4-FDCA from 2,5-FDCA. Thus acetone soluble part was separated, combined together and evaporated under reduced pressure in a rotatory evaporator yielded 2,4-FDCA, which was not 100% qualitative, but not less than 85% purity (from NMR-see FIG. 3) and the investigation is in progress to find the more precise way to get 100% pure compound of 2,4-FDCA.

EXAMPLE 5

Synthesis and Purification of FDCA Methylesters 1.0 g of crude reaction mixture (mainly consisting of 2,4-FDCA, 2,5-FDCA, 2-Furoic acid and a trace amount of 3,4-FDCA) was refluxed in methanolic HCl (1.2 M) (10 ml) at 75° C. for 3 h. After completion of the reaction, the solvent was evaporated in a rotatory evaporator under reduced pressure. The resulting yellow viscous oil was dissolved in ethyl acetate and washed with water (15 ml×2), dried over magnesium sulfate, filtered and the solvent evaporated. Highly purified 2,4-furan dicarboxylic acid methyl ester and 2,5-furan dicarboxylic methyl ester were obtained by using column chromatography separation using 6% ethyl acetate and petroleum ether as eluents. The esters were further recrystallized from methanol.

Although the foregoing has been described in some detail by way of illustration for purposes of clarity of understanding, it will be apparent that various changes and modifications may be practiced within the scope of the appended claims.

What is claimed is:

1. A process for producing a mixture of 2,4-FDCA and 2,5-FDCA by a disproportionation route comprising the following steps:
   a) oxidizing furfural compounds in the presence of catalysts and alkaline solution in order to obtain biobased furoic acid salts, wherein the catalysts are selected from the group consisting of $Au/TiO_2$, Au/C, Au/ZnO, $Au/Fe_2O_3$ or other Au catalysts;
   b) heating the furoic acid salts under stirring in the presence of a metal based catalyst to prepare a reaction mixture and cooling the reaction mixture until room temperature;
   c) collecting furan from the reaction mixture obtained in item (b) in order to obtain the mixture of 2,4-FDCA and 2,5-FDCA;
   d) optionally, filtering off black insoluble material of the reaction mixture obtained in item (c) and acidifying the reaction mixture in order to collect 2,5-FDCA; and
   e) optionally, subjecting the mixture obtained in item 1 (c), to an extraction or other separation method in order to purify 2,4-FDCA.

2. A process for producing 2,4-FDCA and 2,5-FDCA by disproportionation route according to claim 1 wherein an amount of pressure of oxygen used in step 1 (a) comprises from $10^5$ to $5 \times 10^5$ Pa.

3. A process for producing 2,4-FDCA and 2,5-FDCA by disproportionation route according to claim 1 wherein the alkaline solution used in step 1 (a) is chosen from NaOH, KOH, LiOH, $K_2CO_3$ or other alkaline solution.

4. A process for producing 2,4-FDCA and 2,5-FDCA by disproportionation route according to claim 1 wherein the oxidation of step 1 (a) is performed at a temperature of 0 to 50° C. for 1-5 hours.

5. A process for producing 2,4-FDCA and 2,5-FDCA by disproportionation route according to claim 1 wherein the furoic acid salts obtained in step 1 (a) comprise potassium, sodium, lithium or cesium.

6. A process for producing 2,4-FDCA and 2,5-FDCA by disproportionation route according to claim 1 wherein the furoic acid salts are heated in step 1 (b) at a temperature of 220° to 280° C. for 1 to 5.5 hours.

7. A process for producing 2,4-FDCA and 2,5-FDCA by disproportionation route according to claim 1 wherein the metal based catalyst used in step 1 (b) comprises transition metal salts, alkaline earth metal salts, or combinations thereof.

8. A process for producing 2,4-FDCA and 2,5-FDCA by disproportionation route according to claim 7 wherein the metal based catalyst used in step 1 (b) is chosen from $FeCl_2$ or $CdI_2$ or $Zn(OTf)_2$ or $ZnCl_2$ or $ZnI_2$ or mixtures thereof.

9. A process for producing 2,4-FDCA and 2,5-FDCA by disproportionation route according to claim 1 wherein the reaction mixture is acidified in step 1 (d) with HCl until the reaction mixture has a pH of 1-3.

* * * * *